United States Patent [19]

Broggi et al.

[11] 4,127,571

[45] Nov. 28, 1978

[54] PROCESS FOR PREPARING PENICILLINS

[75] Inventors: Renato Broggi; Marco Falciani, both of Milan, Italy

[73] Assignee: Dobfar S.p.A., Milan, Italy

[21] Appl. No.: 859,525

[22] Filed: Dec. 12, 1977

[30] Foreign Application Priority Data

Dec. 16, 1976 [IT] Italy .............................30481A/76

[51] Int. Cl.$^2$ ...................... C07D 49/12; C07D 49/04
[52] U.S. Cl. .................................................. 260/239.1
[58] Field of Search ...................................... 260/239.1

[56] References Cited

U.S. PATENT DOCUMENTS 3,479,338  11/1969  Adams ................................ 260/239.1

*Primary Examiner*—Gerald A. Schwartz
*Attorney, Agent, or Firm*—Oblon, Fisher, Spivak, McClelland & Maier

[57] ABSTRACT

A process for preparing penicillins, in which 6APA is treated with a polar solvent, then with an organic base to give a mixture which is cooled at a temperature lower than −25° C. A cyclic derivative of boron is added to the mixture and the temperature is increased to about 0° C.

An intermediate compound is formed which by treatment first with an acylating agent and then with a mixture of water and alcohol provides a solution containing the penicillin.

5 Claims, No Drawings

PROCESS FOR PREPARING PENICILLINS

This invention relates to a process for preparing penicillins.

It is well known that penicillins can be prepared by several methods from 6APA. According to some of these processes the carboxyl group of 6APA is steadily or temporarily protected by agents of a different nature, which are then removed by hydrolysis or chemical reactions at the completion of the reaction for converting 6APA to the desired penicillins.

For example, U.S. Pat. No. 3,479,338 and British Pat. No. 1,339,605 describe the protection of carboxyl group of 6APA with trimethylxylyl group, which is then removed by hydrolysis.

In the above mentioned type of processes, use is required of basic agents to separate the halogenidric acids released from the acylating agent used.

It is the object of the present invention to provide a process for preparing penicillins from 6APA, by using protecting agents for the carboxyl group of 6APA, which process can be readily and simply carried out, without requiring any use of basic agents.

These and still further objects are achieved by a process, according to which 6APA is treated at room temperature with a polar anhydrous organic solvent selected from the group comprising acetonitrile, tetrahydrofuran, methylene chloride and chloroform, adding a tertiary or secondary organic base selected from the group comprising dialkylamines and trialkylamines, the process being characterized in that the resulting mixture is cooled to a temperature of between −45° C. and −25° C., and has added thereto a cyclic derivative of boron selected from the group comprising ethylene chloroboronate, propylene chloroboronate and phenylene chloroboronate in an amount of at least 2 moles for each mole of starting 6APA, the temperature is increased to about 0° C., thus forming an intermediate compound having the formula

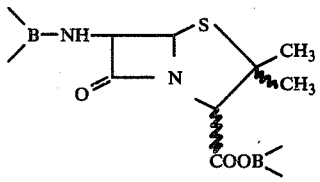

adding at a temperature of between −10° C. and 0° C. an acylating agent selected from the group comprising D(-)-α-amino-α-phenylacetic acid chloride hydrochloride, D(-)-α-amino-parahydroxy-phenylacetic acid chloride hydrochloride, and 1-amino-1-cyclohexancarboxylic acid chloride hydrochloride, then adding at completion of acylation reaction a mixture of water and hydrosoluble alcohol to provide an aqueous solution, from which the penicillin is isolated by known techniques.

The above mentioned cyclic derivatives of boron are well known. For example, preparation of ethylene chloroboronate (i.e., 2-chloro-1,3,2-dioxaborinane) is disclosed by J. A. Blau in J. Chem. Soc. 4116 (1957).

It is important to note that the intermediate compound 1;3;2-dioxaboran-yl-6-(1;3,2-dioxaboran-2-yl-amino) penicillinate can be isolated from its forming reaction medium and then used for completing the reaction, or can be left in the reaction medium without any isolation to complete a continuous process.

In order that the practical methods and characteristics of the process according to the present invention be more clearly understood, some exemplary embodiments of the invention will now be described, as given by mere way of unrestricted example.

EXAMPLE 1

PREPARATION IN TWO STEPS OF 6-[D(-)-α-AMINO-α-PHENYLACETAMIDO ] PENICILLANIC ACID TRIHYDRATE (Ampicillin trihydrate)

12 g 6-amino-penicillanic acid (6-APA) were suspended in 140 ml anhydrous tetrahydrofuran. At room temperature, 15.5 ml triethylamine were dropwise poured into the suspension, thus obtaining a nearly complete dissolution of 6-APA. The suspension was cooled to −40° C., and 92.5 ml of a 1.2 molar solution of 2-chloro-1,3,2-dioxaborinane in tetrahydrofuran were pored. The reaction was exothermic. The temperature was gradually risen to 0° C. in 1 hour and then to +25° C.

The mixture containing triethylamine hydrochloride as a suspension was vacuum evaporated to 90 ml at +25° C. The precipitate was filtered and evaporated to a substantial residue, then suspending with hexane to cause solid crumbling and filtering to obtain 21.2 g of a yellow amorphous powder resulting to comprise a novel molecule, intermediate in the preparation of the penicillin, and which was 1,3,2-dioxaboran-yl-6-(1,3,2-dioxaboran-2-yl-amino) penicillinate. 20.5 g of this novel molecule in the form of amorphous powder were dissolved in 200 ml anhydrous methylene chloride. The solution was cooled to 0° C. and added with 11.4 g of D(-)-α-amino-α-phenylacetic acid chloride hydrochloride, and then the temperature was gradually increased to +25° C. in 2 hours. The solution was cooled again to 0° C. and 200 ml of an aqueous 50% methanol solution were poured. Unmixing was allowed and the organic phase was washed with 50 ml water. The combined aqueous extracts has a highly acidic pH. By means of ammonium hydroxide, pH of solution was brought to 4.8, providing an abundant white precipitate.

The product was filtered, washed with water and isopropanol. The product was vacuum dried at 40° C., obtaining 15.9 g 6-[D(-)-α-amino-α-phenylacetamido] penicillanic acid trihydrate 97.9%, m.p. 206° C. (with decomposition), specific rotation $[\alpha]_D = +290°$ on dry (C=0.25, buffer phosphate pH 4.4), $H_2O$ (K.F.) = 13.85%.

EXAMPLE 2

SINGLE STEP PREPARATION OF 6-[D(-)-α-AMINO-α-PHENYLACETAMIDO ] PENICILLANIC ACID TRIHYDRATE (Ampicillin trihydrate)

21.6 g 6 APA were suspended in 200 ml chloroform. 27.8 ml triethylamine were poured into the suspension, then cooling to −35° C. after dissolution. The solution was added with 181.8 ml drop by drop of a 1.1 molar solution of 2-chloro-1,3,2-dioxaborinane in chloroform. The temperature was increased to 0° C.

The mixture was then portion added with 20.6 g D(-)-α-phenylglicine chloride hydrochloride. The mixture temperature was gradually hrought to +25° C. in 2 hours. The mixture was cooled to 0° C. and 250 ml of an aqueous 50% methanol solution were quickly poured. Unmixing was allowed and the phases were separated. The organic layer was washed with 100 ml water and the combined aqueous extracts were treated with a solution of ammonium hydroxide to pH 4.8.

After stirring for 2 hours at 0° C., the product was filtered, washed with water and isopropanol, and vacuum stove dried at 40° C., obtaining 17.1 g 6-[D(-)-α-amino-α-phenylacetamido] penicillanic acid trihydrate, m.p. 208° C. (with decomposition), 98.1% purity, 14% water contents, and specific rotation $]a[_D = +291°$ on dry.

EXAMPLE 3 PREPARATION OF 6-[D(-)-α-AMINO-p-HYDROXY-α-PHENYLACETAMIDO] PENICILLANIC ACID TRIHYDRATE (Amoxicillin trihydrate)

12 g 6-APA were suspended in 160 ml methylene chloride, and under stirring 15.5 ml triethylamine were poured. The mixture was cooled to −30° C., 100.9 ml of a 1.1 molar solution of 2-chloro-1,3,2-dioxaborinane in methylene chloride were dropwise added, the exothermic behaviour of the reaction was controlled and the temperature was increased to −10° C. 13.1 g D(-)-α-amino-p-hydroxy-α-phenylacetic acid chloride hydrochloride were portion added to the mixture, which was maintained at −10° C. for 30 minutes, then the temperature was gradually increased to +20° C. in 1.5 hours.

The mixture was cooled to 0° C. and 200 ml of an aqueous 50% methanol solution was poured therein.

The mixture was stirred for 15 minutes and allowed to decant, then the phases were mixed and the aqueous layer was filtered.

With ammonium hydroxide pH was brought to isoelectrical point pH = 5, the crystalline mass was stirred at 0° C. for 3 hours and filtered, washing with water and isopropanol.

The product was vacuum dried at 40° C., obtaining 16.1 g 6-[D(-)-α-amino-4-hydroxy-α-phenylacetamido] penicillanic acid trihydrate, m.p. 211° C., 97.5% purity and specific rotation $[α]_D = +296°$ on dry, H$_2$O (K.F.) = 14.1%.

EXAMPLE 4 PREPARATION OF 6-[D(-)-α-AMINO-p-HYDROXY-α-PHENYLACETAMIDO] PENICILLANIC ACID TRIHYDRATE (Amoxicillin trihydrate)

2.16 g 6-APA were suspended in 35 ml methylene chloride. At room temperature and under stirring, 2.8 ml triethylamine were poured into the suspension, the mixture was cooled to −25° C., then introducing 2.45 g propylene chloroboronate as prepared according to the procedure disclosed by J. A. Blau in J. Chem. Soc. 4116 (1957), from boron trichloride and 1.3 propandiole. The mixture temperature was increased to 0° C., then adding by cooling 2.5 g D(-)-α-amino-p-hydroxy-α-phenylacetic acid chloride hydrochloride.

Having controlled the exothermic behaviour of the reaction the mixture was gradually heated to +20° C., cooled again to 0° C., and 20 ml of an aqueous 50% methanol solution were poured. The mixture was allowed to rest and the phases were separated.

The aqeuous phase was purified by treatment with carbon and dicalite. The product was filterd and the solution was added with 2.5 ml ammonium hydroxide to pH 5.1. The product was stirred for 1 hour and filtered. The white product was vacuum dried at 40° C. obtaining a 2.05 g 6-[D(-)-α-amino-p-hydroxy-α-phenylacetamido] penicillanic acid trihydrate, m.p. 210° C., 97.9% purity, specific rotation $[α]_D = +294°$ on dry, and H$_2$O (K.F.) = 13.5%.

EXAMPLE 5 PREPARATION OF 6-[D(-)-α-AMINO-p-HYDROXY-α-PHENYLACETAMIDO] PENICILLANIC ACID TRIHYDRATE (Amoxicillin trihydrate)

4.32 g 6-APA were suspended in 70 ml methylene chloride, then stirring and pouring 5.6 ml triethylamine therein. The mixture was then cooled to −35° C. and 6.4 g phenylene chloroboronate were charged, as prepared according to the procedure disclosed by J. A. Blau in J. Chem. Soc. 4116 (1957) from boron trichloride and pirocatequine. The mixture was heated to −10° C. and at this temperature addition was effected in small portions for 5 g D(-)-α-amino-p-hydroxy-α-phenylacetic acid chloride hydrochloride. After controlling the exothermic behaviour of the reaction, the latter was gradually heated to +20° C., then cooled to +5° C. and quickly pouring into the mixture 35 ml of an aqueous 50% methanol solution. The phases were separated and the acqueous phase was added with a solution of ammonium hydroxide to pH 5. The product was allowed to crystallize under stirring at 0° C. for 2 hours and filtered, then vacuum dried at 40° C. obtaining 4.5 g 6-[D(-)-α-amino-p-hydroxy-α-phenylacetamido] penicillanic acid trihydrate, m.p. 212° C., 97.6% purity, specific rotation $[α]_D = +296°$ on dry, H$_2$O (K.F.) = 13.9%.

EXAMPLE 6 PREPARATION OF 6-(1-AMINO-1-CYCLOHEXAN-CARBOXAMIDO) PENICILLANIC ACID (ciclacylline)

2.16 g 6-APA were suspended in 40 ml acetonitrile. At room temperature and under stirring 1.6 g diethylamine were poured into the suspension. The mixture was cooled to −25° C. and 18.5 ml of a 1.1 molar solution of 2-chloro-1,3,2-diox aborinane in methylene chloride was poured. The exothermic behaviour of the reaction was controlled, then heating to −10° C. The mixture was portion added with 1.8 g 1-amino-1-cyclohexancarboxylic acid chloride hydrochloride. The temperature was held at −10° C. for 30 minutes, then heating to +20° C. After cooling again to 0° C., 20 ml of an aqueous 50% methanol solution were poured into the mixture. The product was allowed to rest and the phases were separated. The organic layer was washed with 10 ml water. The combined aqueous extracts were purified by treatment with carbon and dicalite. The product was filtered and the filtrate added with 15 ml methylisobutylketone. The mixture stirred at 0° C. was added with a solution of ammonium hydroxide to pH 4.7.

The product was allowed to crystallize for 3 hours and filtered. In an amount of 2.2 g the product was in chromatography in a thin layer equal to a standard sample of 6-(1-amino-1-cyclohexancarboxamido) penicillanic acid as dihydrate.

2 g of the product in dihydrate form were suspended in 10 ml of acetone and 0.9 ml of water. The mixture was refluxed for 15 minutes.

3.1 ml methanol were added and reflux was continued for 45 minutes. The mixture was cooled at room temperature and filtered to give 1.4 g of 6-(1-amino-1-cyclohexanecarboxamido) penicillanic acid in anhydrous form with 0.5% water contents, tested by Karl Fischer method.

What is claimed is:

1. A process for preparing penicillins, wherein at room temperature 6-APA is treated with a polar anhydrous organic solvent selected from the group comprising acetonitrile, tetrahydrofuran, methylene chloride and chloroform, adding a tertiary or secondary organic base selected from the group comprising dialkylamines and trialkylamines, and wherein the resulting mixture is cooled to a temperature of between −45° C. and −25° C., and has added thereto a cyclic derivative of boron selected from the group comprising ethylene chloroboronate, propylene chloroboronate and phenylene chloroboronate, in an amount of at least 2 moles of 6-APA, the temperature is increased to about 0° C., thus forming an intermediate compound having the formula

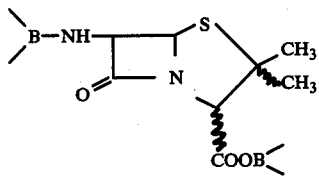

adding at a temperature of between −10° C. and 0° C. an acylating agent selected from the group comprising D(-)-α-amino-α-phenylacetic acid chloride hydrochloride, D(-)-α-amino-p-hydroxy-phenylacetic acid chloride hydrochloride and 1-amino-1-cyclohexancarboxylic acid chloride hydrochloride, finally adding at completion of acylation reaction a mixture of water and hydrosoluble alcohol to provide an aqueous solution, from which the penicillin is isolated by known techniques.

2. A process according to claim 1, wherein as an acylating agent, D(-)-α-amino-p-hydroxy-phenylacetic acid chloride hydrochloride is used to provide, as a penicillin, 6-[D(-)-α-amino-p-hydroxy-α-phenylacetamido] penicillanic acid trihydrate.

3. A process according to claim 1, wherein, as an acylating agent, D(-)-α-amino-α-phenylacetic acid chloride hydrochloride is used to provide, as a penicillin, 6-[D(-)-α-amino-α-phenylacetamido] penicillanic acid trihydrate.

4. A process according to claim 1, wherein, as an acylating a agent, 1-amino-1-cyclohexancarboxylic acid chloride hydrochloride is used to provide, as a penicillin, 6-(1-amino-1-cyclohexancarboxamido) penicillanic acid in dehydrate form.

5. A process according to claim 4, wherein said 6-(1-amino-1-cyclohexancarboxamido) penicillanic acid in dihydrate form is suspended in a mixture of methanol: acetone: water in a ratio of about 10:0.9:3:1, reflux heated, cooled and filtered to give the same compound in anhydrous form.

* * * * *